(12) United States Patent
Snowball

(10) Patent No.: US 9,597,422 B2
(45) Date of Patent: Mar. 21, 2017

(54) DISINFECTION OF PACKAGED ARTICLES

(71) Applicant: Ozonica Limited, Northampton (GB)

(72) Inventor: Malcolm Robert Snowball, Essex (GB)

(73) Assignee: Ozonica Limited (GB)

( * ) Notice: Subject to any disclaimer, the term of this patent is extended or adjusted under 35 U.S.C. 154(b) by 242 days.

(21) Appl. No.: 14/146,155

(22) Filed: Jan. 2, 2014

(65) Prior Publication Data

US 2014/0119991 A1    May 1, 2014

Related U.S. Application Data

(63) Continuation of application No. 13/467,608, filed on May 9, 2012, now Pat. No. 8,641,977.

(30) Foreign Application Priority Data

May 9, 2011   (GB) .................................. 1107692.4

(51) Int. Cl.
*A61L 2/26* (2006.01)
*A61L 2/20* (2006.01)
*A23L 3/3409* (2006.01)
*B65B 55/02* (2006.01)

(52) U.S. Cl.
CPC .............. *A61L 2/26* (2013.01); *A23L 3/34095* (2013.01); *A61L 2/202* (2013.01); *B65B 55/02* (2013.01)

(58) Field of Classification Search
CPC .......... A61L 2/26; A61L 2/22; A23L 3/34095; B65B 55/02
See application file for complete search history.

(56) References Cited

U.S. PATENT DOCUMENTS

| 3,600,126 A | 8/1971 | Hellund |
| 3,971,968 A | 7/1976 | Bachmann et al. |
| 2002/0060189 A1* | 5/2002 | Conrad .................. C01B 13/11 210/739 |

(Continued)

FOREIGN PATENT DOCUMENTS

| CN | 2155368 Y | 2/1994 |
| DE | 19640528 A1 | 4/1998 |

(Continued)

OTHER PUBLICATIONS

Great Britain Search Report for Application No. GB1208102.2 dated Sep. 5, 2012.

(Continued)

*Primary Examiner* — Kishor Mayekar
(74) *Attorney, Agent, or Firm* — Lerner, David, Littenberg, Krumholz & Mentlik, LLP

(57) ABSTRACT

An apparatus for generating ozone inside packaged articles comprises an electrode assembly in which coplanar electrodes are supported along a contact surface. The electrodes are solid state conductive electrodes. These electrodes may be interdigitated and/or arranged with uniform spacing therebetween along a portion of their length. Where the electrodes are straight they may be parallel, but other shapes can also be evenly spaced. In some examples the electrodes are partially insulated and partially exposed. In some examples the electrodes are embedded/potted in an insulator to exclude air spaces from around the electrodes.

15 Claims, 12 Drawing Sheets

(56) References Cited

U.S. PATENT DOCUMENTS

| | | | |
|---|---|---|---|
| 2004/0241057 A1* | 12/2004 | Goodley | ............ C01B 13/11 |
| | | | 422/186.07 |
| 2006/0042545 A1 | 3/2006 | Shibata et al. | |
| 2012/0213664 A1 | 8/2012 | Diver et al. | |
| 2014/0044595 A1* | 2/2014 | Keener | ................ A61L 2/14 |
| | | | 422/23 |

FOREIGN PATENT DOCUMENTS

| | | |
|---|---|---|
| DE | 19814865 C2 | 9/2000 |
| EP | 1726314 A4 | 9/2008 |
| GB | 2457057 A | 8/2009 |
| JP | 2004209188 A | 7/2004 |
| WO | 02071438 A3 | 3/2003 |
| WO | 2009040130 A1 | 4/2009 |
| WO | 2010116191 A1 | 10/2010 |
| WO | 2011055113 A1 | 5/2011 |
| WO | 2011116984 A2 | 9/2011 |
| WO | 2011137359 A1 | 11/2011 |

OTHER PUBLICATIONS

International Search Report for Application No. PCT/GB2012/051017 dated Feb. 4, 2013.

* cited by examiner

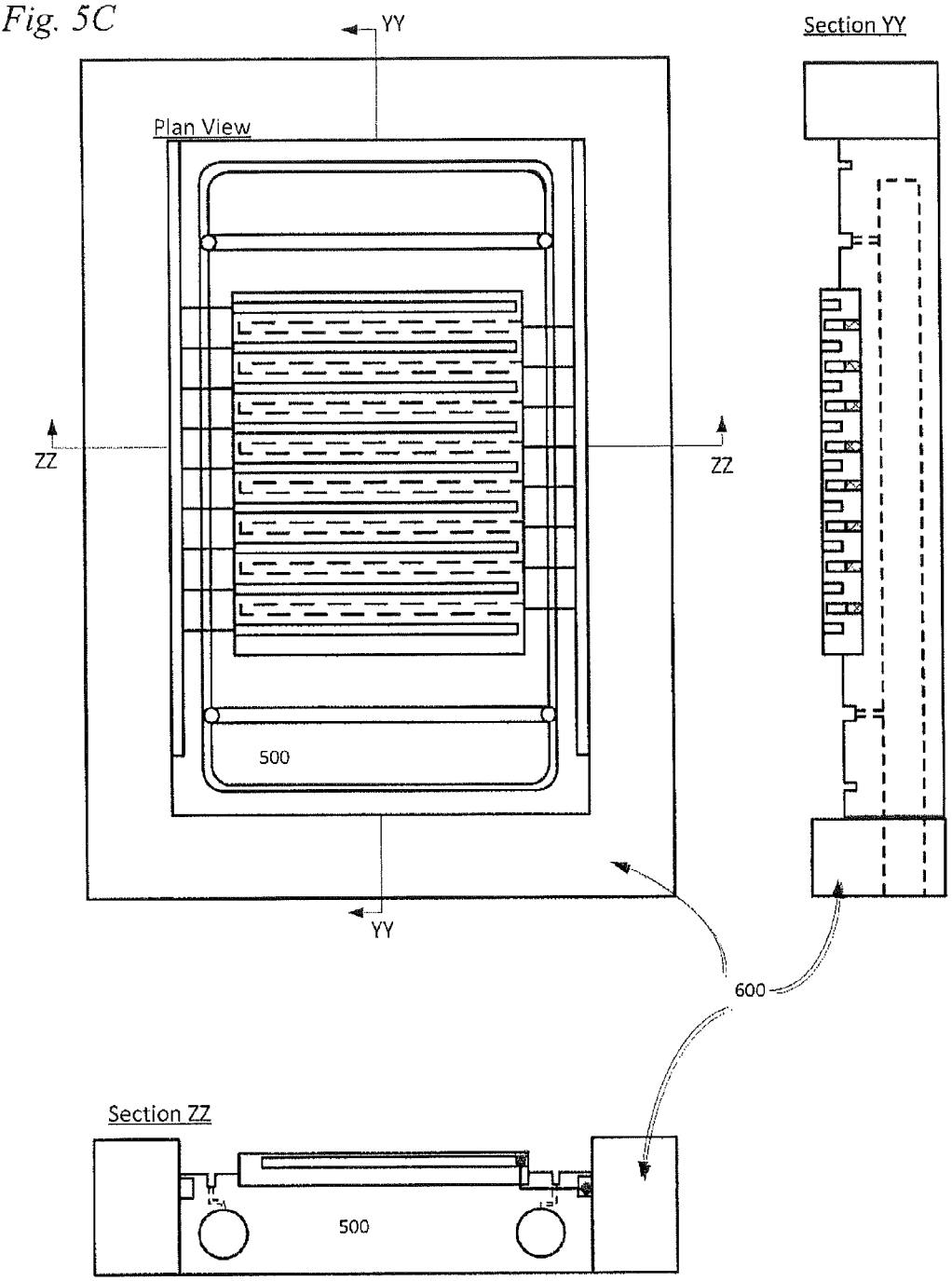

DISINFECTION OF PACKAGED ARTICLES

CROSS REFERENCE TO RELATED APPLICATIONS

The present application is a continuation of U.S. patent application Ser. No. 13/467,608, filed on May 9, 2012, which claims the benefit of and priority to United Kingdom Application No. GB1107692.4, filed May 9, 2011, the entire contents of which are hereby incorporated by reference.

BACKGROUND OF THE INVENTION

This invention relates a method and an apparatus for the sterilisation and/or disinfection of packaged articles such as packaged food and drink products.

The shelf life of food is substantially shortened due to the presence of micro-organisms in the food, which can cause the food to deteriorate. Not only does shelf life affect the economic viability of food producers but it has a direct effect on public health, since the presence of certain micro-organisms in food can be hazardous if the food is ingested. These problems can be exacerbated if the food is not kept sufficiently refrigerated, since the micro-organisms in the food can multiply rapidly.

In order to overcome the above-mentioned problems, it has been proposed to pasteurise food. However, a disadvantage of pasteurisation is that the process is lengthy and can only be used on certain types of food. Furthermore, the pasteurisation process affects the taste of the food and is costly to perform, since it uses a substantial amount of energy, a great deal of which is discharged into the working environment. In one known method, the food is packaged in an atmosphere which inhibits the fast reproduction of micro organisms. One such an approach is to package the food product within a carbon dioxide atmosphere. This has proved to be difficult to control, environmentally unfriendly and expensive to run. GB2457057 discloses an alternative method in which the food product is disinfected by irradiating it with UV light through its sealed packaging. This method requires the packaging material to pass the disinfection wavelengths (around 260 nm) at high efficiencies, otherwise high power is required to get sufficient UV intensity into the package to disinfect the food. Present packaging materials are poor transmitters of these UV wavelengths and therefore special packaging materials need to be used. Such packaging materials are expensive and necessitate modifications to the existing packaging processes, which mean that the whole food industry will have to change its packaging equipment or develop a whole new family of packaging materials.

In order to achieve adequate disinfection inside a sealed package it is necessary that all of the product surfaces are irradiated with the UV light. This is extremely difficult to achieve, for example in the case of sliced meat or cheese where the light will not reach between the slices therefore the disinfection effect will be marginal and therefore the shelf life will not be improved. The method also suffers from a susceptibility to dust and dirt, since the UV lamps must be clean at all times and it will be appreciated that the general environment in the food processing industry does not lend itself to this. This method also has the added disadvantage that the UV light must have a clear "window" to penetrate the package i.e. no labelling or printing on the package. This makes the packaging process inflexible and forces packaging process redesign.

It is well known that ozone is a highly oxidising gas, which is a very efficient disinfector of micro-organisms. Ozone has a very short life (about 20 minutes) before it naturally reverts back to oxygen and therefore ideally suited for extending the shelf life of food sold in sealed packages and for killing other harmful micro-organisms that may be contained in the food such as *e-coli*.

GB2457057 also discloses a method in which the food product is further disinfected in its sealed package by creating ozone inside the package using UV light of ozone producing wavelengths. Ozone, being a gas with very efficient disinfection properties, will permeate everywhere inside the sealed package and will therefore disinfect the product. Unfortunately this method suffers from the same disadvantages as the above-mentioned UV disinfection method, in that the packaging materials to pass such UV wavelengths are even more special and are expensive to buy and process. Also, the ozone producing wavelengths are in the vacuum UV range (around 185 nm) and known packaging materials pass these wavelengths inefficiently and hence are energy inefficient.

In practice, the amount of ozone produced by UV methods is relatively low and is significantly affected by atmospheric humidity. Accordingly, in a fixed flow process where the time to dose each package is fixed, it is very difficult to get a consistent ozone dose. This method also produces nitrous oxide as a by product from the air inside the package which is undesirable, since nitrous oxide combined with water produces nitric acid which will damage the product. Another drawback to this approach is that there is an amount of unwanted ozone produced in the air spaces surrounding the UV lamp, which must be neutralized as free ozone is a regulated substance because the presence of ozone in the atmosphere presents a health hazard.

This method also has the added disadvantage that the UV must have a clear window to penetrate the package i.e. no labelling or printing on the package. This makes the packaging process inflexible and forces packaging process redesign. Another known method of sterilising food comprises creating ozone inside a sealed package using a conventional corona discharge methods. This entails a metal electrode placed either side of the sealed package and a high voltage ac supply connected to the electrodes. The high voltage creates a corona discharge between the electrodes, which then converts some of the oxygen in the air in the package to ozone.

Whilst this method avoids some of the problems with the UV irradiation method, it still suffers from some serious shortcomings. The method uses metal electrodes, which heat up to a significantly high temperature during operation and therefore need to be force cooled. These electrodes are in close proximity to the packaging material and hence have to be cooled to less than 70 degrees centigrade, otherwise the packaging material is degraded. This usually requires water cooling with its associated pumping and heat exchanger systems. This method is a discharge system, which means that electrons are discharged between the electrodes under high voltage conditions: as a consequence there is erosion and hence deterioration of the electrodes leading to short electrode life and hence poor reliability. Discharges of this technology are uncontrolled avalanche types, which not only penetrate the packaging material but also the product and can be very detrimental to some products. This method usually cannot be repeated more than once as the product deterioration due to repeated corona discharge is unacceptable. Corona discharge whilst producing medium to high levels of ozone also suffers from inconsistent ozone production due to atmospheric humidity and worse produces high levels of nitrous oxide from the nitrogen in the air inside the package. As a consequence this method is usually confined to applications where the packaging environment is pure oxygen and hence no nitrous oxide is formed. To package product in oxygen is both difficult to control and expensive.

Our earlier publication WO2010/116191 provides an advantageous method and apparatus for generating ozone within a package using gas filled electrodes. We have now found that it is possible to provide useful ozone sterilization using elongate solid state electrodes and have provided a number of other improvements to reduce power requirements and increase effectiveness.

BRIEF SUMMARY OF THE INVENTION

In an aspect there is provided a package disinfection apparatus comprising two solid state conductive elongate electrodes configured to receive an alternating voltage to enable generation of ozone between the electrodes such that, in use applying the electrodes to a package converts oxygen to ozone within said package.

In an embodiment the electrodes are substantially covered with an insulating material. In an embodiment one electrode is covered with an insulating material and the other comprises an exposed electrically conductive region. In an embodiment the electrodes comprise distributed impedances, and the electrodes may comprise a plurality of raised regions distributed along their length. For example the electrodes may comprise a coiled conductor and the raised regions are provided by the turns of the coil. The raised regions may comprise ridges. Adjacent raised regions may be coupled by a series impedance. Typically the transverse cross section of the electrodes is square however they may also be round, or rectangular in cross section.

Preferably the electrodes are arranged such that, in use each electrode comprises a feed end for receiving electric current and a second end and the electrodes are arranged generally alongside each other and in opposition such that the feed end of each of the two electrodes is arranged in apposition to the second end of the other of the two electrodes.

Preferably the apparatus comprises an electrode support for supporting the electrodes to enable them to be brought into contact with a package. Preferably the apparatus comprises a means for urging the electrode into contact with a package to be disinfected. The means for urging and/or the support may comprise a suction coupling to couple a suction source to a contact surface of said electrode support. The apparatus may also comprise a sensor for sensing pressure at the contact face of the electrode support to enable control of the current based on the pressure.

The electrode support may comprise a seal or sealing member arranged on or around said contact surface. Preferably the electrodes are arranged in a substantially coplanar configuration and they may be substantially parallel. One or more electrode may be arranged in an insulating sheath. Typically the electrodes are potted in an insulating material to exclude air gaps from around the electrodes. The insulating material may comprise a cured material which is introduced into the sheath in liquid form.

Typically the apparatus is configured to convert oxygen to ozone by generating a plasma. He apparatus may be configured such that capacitive coupling between the electrodes promotes the conversion of oxygen to ozone within said package by means of the electric field between said electrodes. The package disinfection apparatus may comprise a low voltage AC power supply and a first step up transformer coupled to a first one of the two electrodes and a second step up transformer coupled to the other of said electrodes so that said transformers provide a power supply to said electrodes of relatively higher voltage than said low voltage AC power supply. Preferably each transformer is arranged in close proximity to the electrode to which it supplies power. The transformers may be coupled to the electrodes by shielded cables.

The package disinfection apparatus may comprise a current sensor for sensing current flow between said electrodes in order to detect an over current condition and control means for preventing operation of the packet disinfection apparatus in the event an over current condition is detected.

Preferably the apparatus is adapted for processing a plurality of packaged articles and comprises means for adjusting the voltage applied to said electrodes and/or the length of time for which said voltage is applied based on the type of article.

The electrodes are preferably arranged less than 5 mm apart, preferably less than 3 mm apart, preferably substantially 2 mm apart or less.

There is also provided a calibration method for a package disinfection apparatus comprising: irradiating a packaged article for a first time interval at a first voltage level to produce ozone in said package and testing the contents of said package to determine a quantity of ozone in the package; and, in the event that the quantity of ozone exceeds a threshold level storing an association between an identifier of the type of article and at least one of the time interval and the voltage level in a memory.

Preferably irradiating comprises using a package disinfection apparatus or electrode assembly according to any one described herein.

In an aspect there is provided a packet disinfection electrode assembly for generating plasma inside a package comprising a packaged article and an air space, the electrode assembly comprising: a dielectric head having a contact surface for contacting said package; and at least two electrically conductive electrodes distributed about the contact surface, wherein a first one of the two electrodes is insulated and an electrically conductive region of the second of said electrodes is exposed near the contact surface. This use of both exposed and insulated electrodes has been found to enable packages to be disinfected using substantially lower power.

In some possibilities the exposed electrode may be earthed.

Preferably the spacing between adjacent edges of the first and second electrode is even along at least a portion of the length of the edges. This has the advantage of enabling reproducible and stable production of plasma in well defined regions adjacent the contact surface. In some possibilities the spacing between adjacent edges along the portion comprises the distance of closest approach of the edges and this/these portion(s) may be continuous in extent or may be broken or discontinuous and/or spread in a number of portions along the electrodes. In some possibilities the spacing between adjacent edges of the first and second electrode is less than 20 mm, preferably less than 15 mm, preferably less than 10 mm. In some possibilities the spacing is less than 5 mm, and may be between 1 mm and 4 mm.

In some cases the electrodes are elongate and have a major dimension and a minor dimension. Preferably the electrodes are aligned along their major dimension and are less than 15 mm wide along their minor dimension. Preferably they are less than 10 mm, preferably less than 5 mm wide. This has the advantage of enabling more plasma creating regions to be provided in a package of fixed size than would be possible where broader electrodes are used.

In some possibilities the first electrode is provided by a first plurality of electrodes and the second electrode is provided by a second plurality electrodes. The first plurality of electrodes may be interleaved with the second plurality of electrodes so that alternate electrodes are insulated whilst the respective other alternate electrodes comprise exposed conductive regions. This has the advantage of reducing the size of the electrode assembly and still further reducing the power required to establish a plasma inside a packaged article.

Preferably the contact surface of the head stands proud of the body by at least 0.2 mm, still more preferably at least 0.4 mm, or at least 0.5 mm. In some possibilities the contact surface is proud of the body by less than 10 mm, preferably less than 8 mm, or less than 5 mm, or less than 3 mm. This has the advantage of enabling the contact surface to be urged into close contact with the wall of a flexible package to deform the package without overstretching the package and/or whilst also enabling the package to be drawn tightly onto the shoulders of the body to exclude air from between the contact surface and the package. Preferably the body comprises a dielectric, e.g. a ceramic such as shapal.

Preferably the body comprises shoulder portions that surround the head to engage with said package such that when, in use, the contact surface is urged into contact with a flexible package, the shoulders are configured to engage with such regions of said package as may overlap the shoulders from the contact surface.

The shoulder portions may comprise a channel that can be coupled to a suction source so that in use the channel can be used to evacuate air from the space between a package and the electrode assembly. The channel may be arranged so that, when in use an electric potential difference is applied between the first electrode and the second electrode, the channel does not coincide with the regions of strongest electric field. This may be achieved by ensuring that the channel is spaced from the electrodes of the contact surface by at least 2 mm. The body may comprise a suction coupling, and a vent passage to provide fluid communication between the suction coupling and the channel. Similarly it is may be important that the suction coupling and/or the vent passage are arranged so that, when in use an electric potential difference is applied between the first electrode and the second electrode, they do not coincide with the regions of strongest electric field. Again, one way to achieve this is to ensure that the vent passage and/or the suction coupling are spaced from the electrodes of the contact surface by at least 2 mm. Greater or smaller spacing may be used.

The electrode assembly may be used in an apparatus comprising a mechanical bias adapted to urge the contact surface against said package with a selected force. In some cases the apparatus comprises a sensor configured to sense the back pressure generated by urging the package against the contact surface and a controller configured to control the mechanical bias based on the sensed back pressure. This has the advantage that the package can be urged into close contact with the assembly without risking damage to the package. Preferably the selected force is determined by a setting of the controller, and preferably this setting is programmable.

The electrodes may be elongate and may comprise a reactive and/or resistive impedance. In some possibilities the electrodes may be arranged so that their impedance is spatially distributed across the area of the contact surface. For example, the electrodes may comprise coils.

In some possibilities the coils are embedded in the head and conductive regions of the second electrode are exposed at or near the contact surface. In some possibilities the second electrode is recessed from the contact surface and in some possibilities the second electrode is flush with the contact surface. The coils may comprise a round cross section but may comprise at least one straight side or be square or rectangular.

The electrodes may be arranged as interdigitated elongate fingers along the contact surface. Preferably the first electrode lies beneath the contact surface and is insulated from the surface by the dielectric of the head. The first electrode is preferably insulated from the contact surface by a thickness of dielectric of at least 0.1 mm, preferably at least 0.2 mm or 0.3 mm. In some possibilities the first electrode is insulated from the contact surface by a thickness of dielectric of less than 2 mm, preferably less than 1.5 mm, preferably less than 1 mm. The dielectric preferably comprises ceramic and in some cases comprises shapal.

Although the electrodes may be straight, in some cases they may also be arranged in other shapes such as serpentine configurations or spirals along the contact surface. In some examples the electrodes are arranged along the contact surface to define the boundaries of concentric laminae. The laminae may be selected from the list comprising one of: circular; elliptical; square; polygonal rectangular; and irregular and the electrodes may define closed boundaries or they may define non-continuous open boundaries.

In an aspect there is provided a method of disinfecting a packaged article comprising providing a packaged article, wherein the package includes an airspace, arranging the package adjacent an electrode assembly, urging the electrode assembly into contact with the package and applying electric power to the electrodes for a selected duration, wherein the electric power is at least 30 Watts and less than 250 Watts and the duration is selected so as to generate at least 2 ppm of ozone in the airspace of the package, preferably in which the duration is at least 0.1 seconds and optionally less than 10 seconds.

Preferably the duration is at least 0.2 seconds. In some possibilities the duration is less than 6 seconds. In some possibilities the duration is at least 0.4 seconds and less than 2 seconds. Although in some cases it is less than 250 Watts, in others the power may be up to 350 Watts. In some possibilities the power may be less than 200 Watts. In some possibilities the power is at least 50 Watts. Generally, the power and/or duration may be selected based on the quantity of air contained in the package so as to generate at least 2 ppm of ozone. The power and duration may be selected based on the quantity of air contained in the package so as to generate no more than 100 ppm of ozone. In some possibilities the power and/or duration may be selected based on the quantity of air contained in the package so as to generate less than 80 ppm of ozone in the airspace.

In examples the electrode assembly comprises at least two electrodes spaced by a distance of at least 0.2 mm. In some cases the interelectrode spacing is at least 0.5 mm and not more than 20 mm, or not more than 5 mm along a portion of their lengths. In some cases applying electric power comprises applying an alternating voltage of at least 5 kV r.m.s amplitude between at least two electrodes of the electrode assembly. Where the spacing is less than 1 mm, for example 0.5 mm or less, then the applied voltage may be between 1 kV and 5 kV, for example between 2 kV and 4 kV.

Advantageously, using more closely spaced electrodes enables lower voltages to be used to generate plasma.

Preferably, the electromagnetic field creates cold plasma which is energetic enough to convert oxygen in air into ozone and other reactive oxygen based species. In use, a sealed package containing the product is placed in close proximity to the gas filled electrodes, such that the electromagnetic field generated by the gas filled electrodes penetrates through the wall of the sealed package forming cold plasma from the trapped air inside the sealed package. This cold plasma comprises ozone and other reactive oxygen based species which have a high oxidising potential and kill all micro organisms in contact with the ozone and reactive species resulting in the disinfection of the product as well as the interior of the sealed package. The present invention efficiently creates ozone and other oxygen reactive species inside a sealed package without any of the above mentioned problems of existing apparatus. We have found that distributed impedance with an insulated electrode reduces electrode erosion and hence promotes long life and high reliability. The apparatus is also insensitive to humidity and dust. I have found that nitrous oxide production is also virtually eliminated using this form of ozone production.

Furthermore, the use of plasma creates oxidising species which have a higher oxidising potential than ozone and therefore are more efficient at killing microorganisms.

Since the invention creates a plasma, it does not involve discharge inside the package therefore there is no harmful discharge through the product. The apparatus is insensitive to package decoration such as labelling or printing and does not deteriorate the decoration. Also, unlike corona discharge this process can be repeated without packaging or product degradation.

Preferably means are provided for directing the generated electromagnetic field towards the product to be sterilised.

Preferably each electrode is elongate and is preferably curved, coiled, bent or otherwise non-linear along its length. Alternatively, each electrode may comprise a plurality of interconnected linear sections. Preferably each electrode is generally planar, said field directing means being arranged to direct the electromagnetic field perpendicular to said plane towards the product to be sterilised. Preferably the electrodes generally extend side-by-side along their length and are preferably separated by a substantially uniform gap. Preferably the electrodes are coated with glass or some other suitable nonconducting material.

Preferably said field directing means extends on one side of the electrodes and comprises a ferromagnetic material. Preferably the material is ferrite or a ferrite composite material which encourages the electromagnetic field to be projected in a single direction. This produces a concentrated electromagnetic field substantially in one direction of the gas filled electrodes. In use, the opposite side of the gas filled electrodes is placed in contact with one of the faces of the sealed package: the electromagnetic field then passes through the wall of the sealed package and thereby maximises the electromagnetic field and hence the cold plasma inside the sealed package.

Preferably said field directing means at least partially extends between the electrodes and preferably comprises a surface which is profiled to received said electrodes. The field directing means has two added benefits: Firstly, it constrains the electromagnetic field in one direction and prevents it from creating unwanted ozone from the air surrounding the gas filled electrodes in all but one direction. Secondly, it prevents any heating effects in closely positioned metal due to electrical induction effects. Preferably the electrodes are contained within an open-fronted cavity preferably defined by said field directing means. Preferably, the electrodes extend in a plane parallel to the front of the cavity. Preferably the cavity comprises a side wall or walls which extend around the electrodes and which are arranged to seal against the packaging of the product to be sterilised.

Preferably means are provided for evacuating air or other gas from said cavity when the latter is sealed against the packaging of the product to be sterilised, the suction helps to form a tight seal between the wall(s) of the cavity and the packaging material. The packaging material is thus drawn tight against the open front of the cavity allowing a near air free connection, thereby minimising unwanted generation of ozone in the interface between the gas filled electrodes and the sealed package.

Preferably said high voltage generation means produces voltages pulses in the range of 1 kV to 50 kV and/or AC current. Preferably said high voltage generation means produces pulses of high voltage in the range 5 ns to 100 ms duration.

Preferably said high voltage generation means is arranged to produce pulses of variable magnitude, variable width and/or variable repetition rate, so that the cold plasma formation can be substantially controlled and a wide range of sealed package production rates can be accommodated.

Preferably the apparatus comprises a sensor for monitoring the electromagnetic field, the sensor being connected to means arranged to vary the output parameters of said high voltage generation means. In this way, the high voltage generation means can accept a feedback signal from the electromagnetic field sensor and can automatically adjust the magnitude of the high voltage pulses and the other pulse parameters, in order to adjust the electromagnetic field and maintain it at a constant level. This ensures constant ozone production package to package.

Preferably said high voltage generation means is arranged to produce voltage pulses of opposite polarities and to apply said pulses to respective electrodes. Preferably the apparatus comprises means for agitating or otherwise moving the product to be sterilised: the products may be irradiated with said electromagnetic field before, after and/or during said agitation. Preferably the agitation means is arranged to at least partially rotate the package. This approach encourages the disinfection gas to quickly permeate through the package and get to all surfaces. Preferably the apparatus is arranged to irradiate successive products. Preferably the apparatus is arranged to successively irradiate the same product.

There is also provided an method of sterilising a packaged product, the method comprising placing a package containing said product in proximity to a pair of elongate solid state electrodes, generating a high voltage between the electrodes sufficient to create a high electromagnetic field therebetween, and allowing the field to irradiate and penetrate the package so as to create ozone therein.

Preferably a cold plasma field is generated which extends within said package and creates ozone. Preferably the generated electromagnetic field is directed towards the product to be sterilised. Preferably the electrodes are contained within an open-fronted cavity, the cavity being sealed against the packaging of the product to be sterilised. Preferably air or other gas is evacuated from said cavity when the latter is sealed against the packaging of the product to be sterilised. Preferably the product to be sterilised is moved or agitated before, after and/or during said irradiation.

In one example opposed coil wound electrode pairs comprise capacitive and inductive impedance being substantially distributed equally along the electrode pair and are operable to form a uniform stable plasma. This and the fact that the electric field and hence the plasma forms filaments across discrete high spots on the coiled electrodes means that the impedance of the coil pair is substantially constant along the length of the electrode pair. This constant impedance not only allows multiple electrode pairs to be used in an array (head) but also allows multiple electrode pairs (heads) to be used in parallel, powered from a single power supply.

BRIEF DESCRIPTION OF THE DRAWINGS

Embodiments of the present invention will now be described by way of example only with reference to the accompanying drawings, in which:

FIG. 3B shows a pair of electrodes such as those shown in FIG. 3a;

FIG. 5C shows the electrode assembly of FIG. 5B with a peripheral seal;

DETAILED DESCRIPTION

Figure 1:
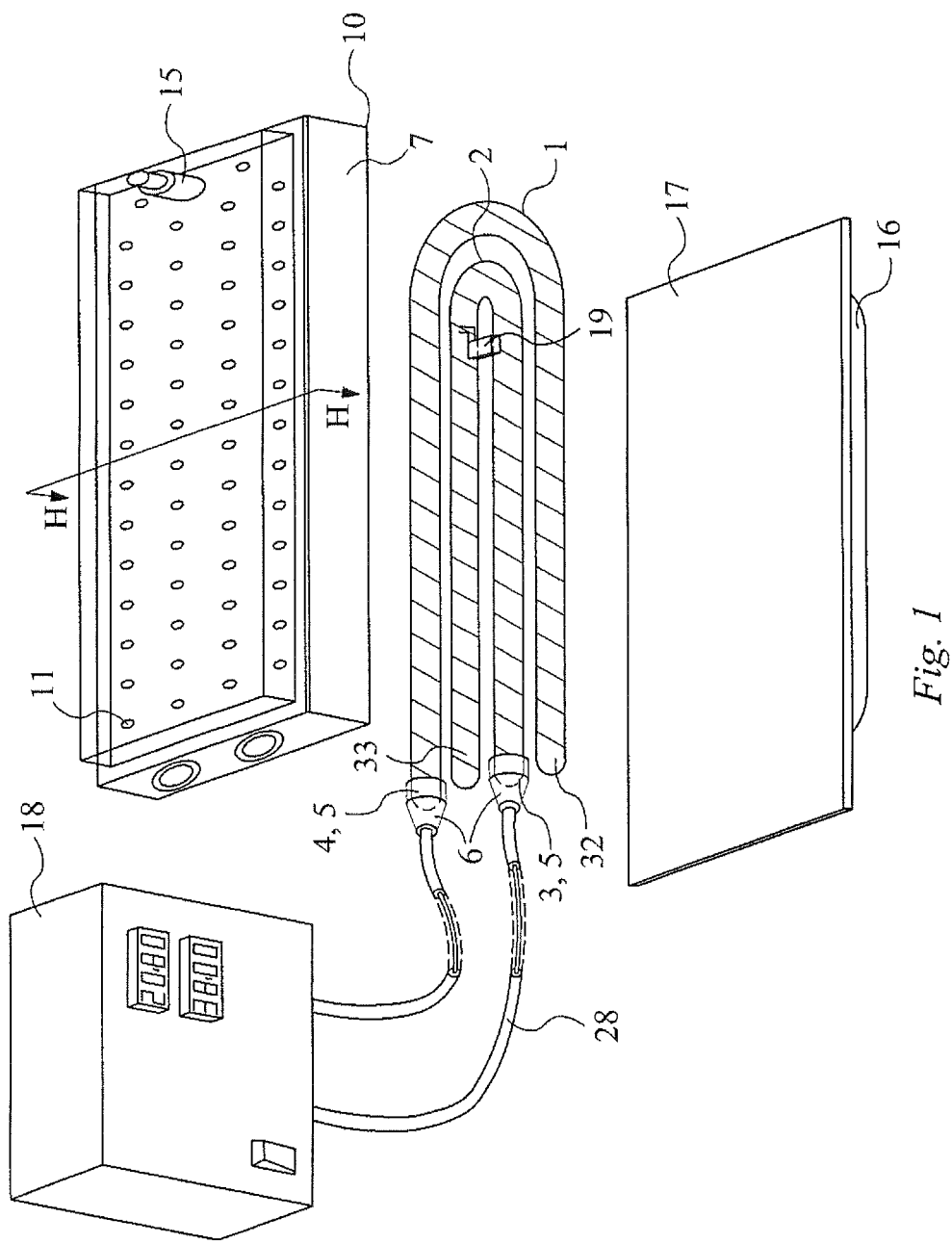
FIG. 1 is an exploded perspective view of a disinfection apparatus.
Figure 2:
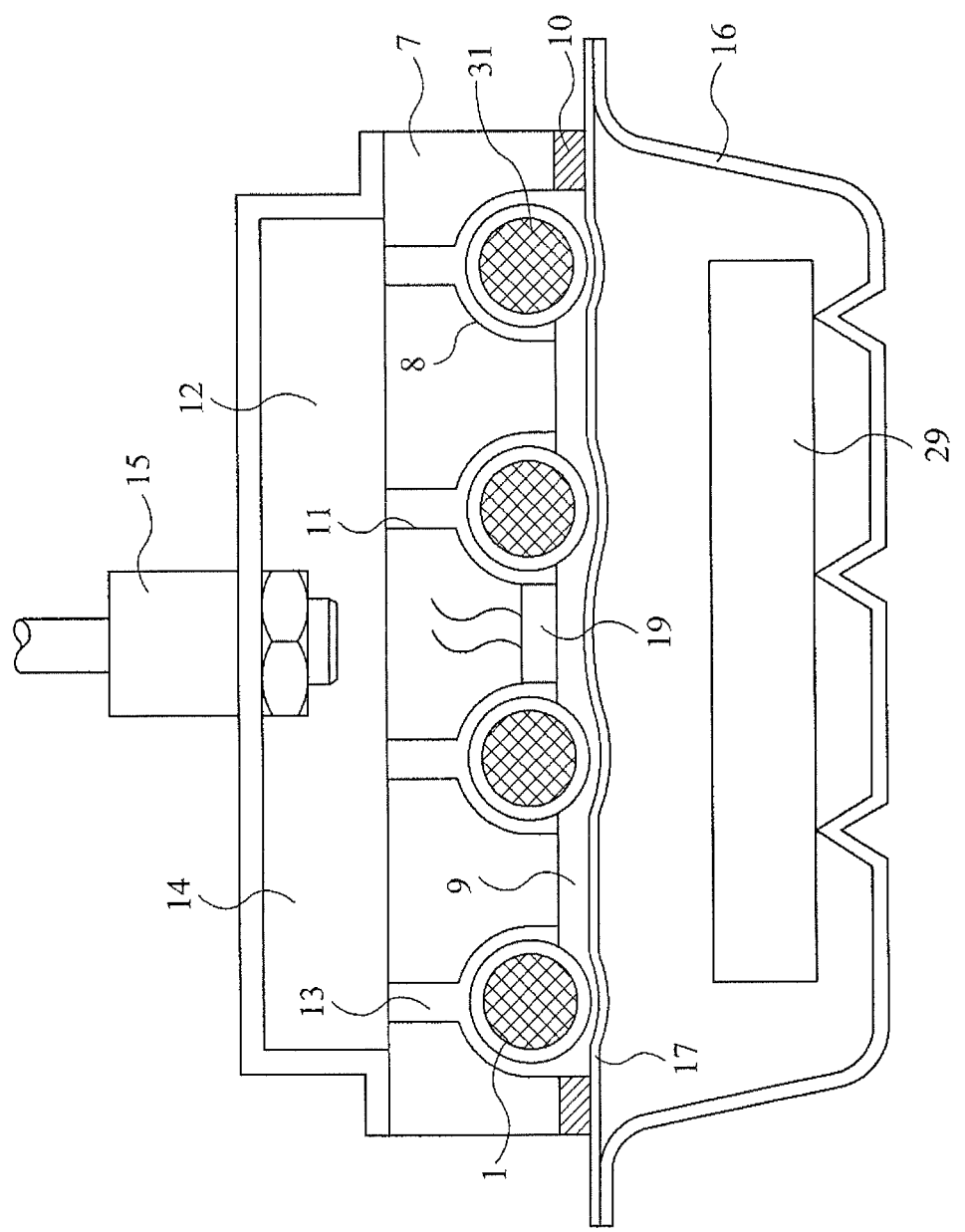
FIG. 2 is a sectional view along the line Il-Il of FIG. 1.

Referring to FIGS. 1 and 2 of the drawings, there is shown disinfection apparatus comprising two solid state conductive electrodes 1, 2. The electrodes 1, 2 extend side-by-side along their length and are separated by a substantially uniform gap.

The electrodes 1, 2 are mounted against a reflector 7 which has a front surface, which is profiled to receive the electrodes 1,2. A portion of the reflector 7 extends between each electrode. The reflector 7 is made from a ferromagnetic material such as ferrite or a ferrite powder and resin mixture to encourage the electromagnetic field generated by the electrodes 1,2 to project or concentrate substantially forwardly. The reflector 7 comprises a depending peripheral sidewall provided with a seal 10, which together define a cavity 9 in which the electrodes 1,2 are recessed. The seal 10 is formed of a material which is both flexible and ozone resistant, such as silicone rubber or viton.

In practice a typical production line may have several streams of packaged product and employ one electrode head per product stream i.e. a line of several heads positioned across the product streams. The packages will be marshaled such that they will line up together under the line of heads and the heads will contact the packages and form an intimate contact with the head under suction. The heads will then be energized to form the cold plasma inside the package.

This approach is fine as long as each head makes intimate contact with the package (good suction) and that the head's insulation integrity is intact i.e. the head and electrodes are not defective. In the event that the head has not made intimate contact with the package then when energized risks converting any oxygen in the air between the head and package or oxygen in the air around the head into ozone. This would potentially endanger process operators.

A vacuum pump or other device (not shown) is provided to draw air through the reflector 7 via apertures into a chamber 14 mounted to the rear of the reflector 7. The chamber 14 is connected to the vacuum pump or other device via a duct 15. The wall of the chamber 14 is preferably formed of a non-conducting material such as plastics.

A sealed package 16 containing the article to be sterilised is positioned in close proximity to front (lower) face of the cavity 9 such that the edges of the package line up with the seal 10. With the sealed package 16 so positioned, suction is applied to duct 15 to produce a tight seal between the sealing film 17 of the sealed package 16 and the to front (lower) face of the cavity 9. The air is substantially removed from the interface between the package 16 and the electrode assembly, which minimises any unwanted ozone outside the package.

The head is fitted with a vacuum switch coupled to detect a vacuum within the seal 10 to detect the integrity of the intimate contact between the head and the package then the head can be prevented from being energized and the none-ozonated package can be removed further down the process. If this problem occurs frequently then the stream for this head can be automatically diverted and redistributed to other streams. This keeps the production running albeit at a slight reduced rate.

A high voltage pulsed dc power supply 18 is provided to ionize the neon gas inside the interior 33 of the electrodes 1, 2. The power supply 18 comprises outputs across which the voltage is applied, the outputs being connected to the metal contacts 5 on respective electrodes 1,2 via the high voltage wires 28.

Preferably the high voltage dc power supply 18 is arranged to produce pulses of variable magnitude, variable pulse width and variable pulse repetition rate to enable the electromagnetic field strength to be controlled.

The high voltage pulses ionises the neon gas 31 in the electrodes 1,2 which then creates an electromagnetic field to form around and between the discharge tubes 1,2 and through the sealing film 17 of the sealed package 16. This electromagnetic field is energetic enough to break down the oxygen in the air inside the sealed package 16 to produce cold plasma containing ozone and other highly reactive oxygen species. Any micro-organisms inside the sealed package 16 are killed on contact by the ozone and other disinfecting species in the cold plasma.

Means are provided to automatically control the electromagnetic field strength and hence improve the package to package disinfection consistency by providing a field strength sensor 19 in close proximity to the electrodes 1,2. The sensor 19 converts the field strength measurement to a signal which is fed into the high voltage power supply 18. The high voltage power supply 18 automatically adjusts one or more of its three variables i.e. pulse magnitude, pulse width and pulse repetition rate to maintain constant electromagnetic field strength from the electrodes 1,2. This technique also allows a wide range of packages to be disinfected from one electrodes assembly.

The voltage output by the power supply 18 is always sufficient to ionise the gas in the electrodes 1,2 even when the pulses are not produced: in this manner the electrodes are kept in a state where they can be quickly energised by the pulses to produce the plasma.

Figure 3A:
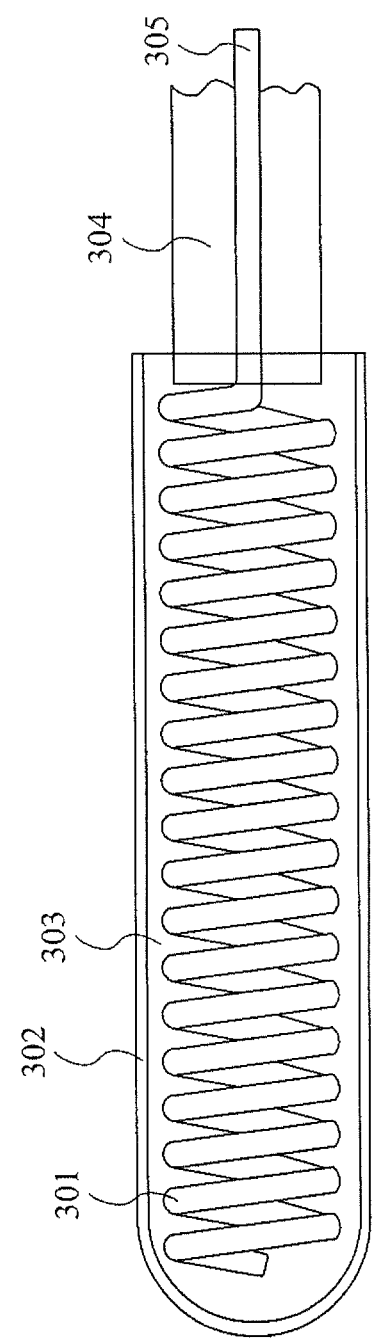
FIG. 3A is a view of a coil wound electrode suitable for use in the embodiment shown in FIGS. 1 and 2.

FIG. 3A shows a part sectioned drawing of an electrode 301 covered by an outer insulating sleeve 302. The interior of the sleeve 302 provides a cavity which is potted with an insulating material which acts to hold the coiled electrode in place within the sleeve.

In FIG. 3A the electrode 301 is in the form or an open helix, much like a compression spring, which is close wound but with spaces between the turns. One end of the helix is open and the other end is formed into a centrally positioned straight wire which forms an electrical connection 305 for applying an electric potential to the electrode. The electrical connection 205 is insulated by an insulating member.

The helix is formed with 25 s.w.g (approximately 0.508 mm) tinned copper wire and the turns of the coil are preferably uniformly spaced.

The length of the coil may vary, however the inventor in the present case has found that plasma may be produced with long electrodes or short electrodes but that, as the surface area of the electrode increases the power to produce and maintain a plasma between a pair of electrodes increases. The coil can be any cross section but the preferred shape of the coil is square or rectangular.

The outer insulating sleeve 302 covers the coil 301 and overlaps it by approximately 6 mm. The material of the sleeve must be an insulator and be highly resistant to erosion caused by the cold plasma. Suitable materials are Aluminium Nitride, Macor, Aremcolox, Shapal, Boron Nitride and Borosilicate glass as well as others.

The outer sleeve can have a domed or flat end and the coil is slid into the inside of the insulating sleeve. The preferred shape of the outer insulating sleeve is square or rectangular such that when it is placed into an array it forms a suitable surface on which the packaging material can be attached by suction.

The inside cavity of the insulating sleeve 302 is potted with an insulating material 303. Preferably the material is introduced to the sleeve in liquid form which subsequently cures to provide a substantially solid material. This has the advantage that, whilst the material is in its liquid state air inside the sleeve can be floated out. When the potting insulator 303 is cured the coil 301, insulating sleeve 302 and the electrode insulation 4 are held rigidly in place which makes the electrode assembly substantially robust.

Figure 3B:
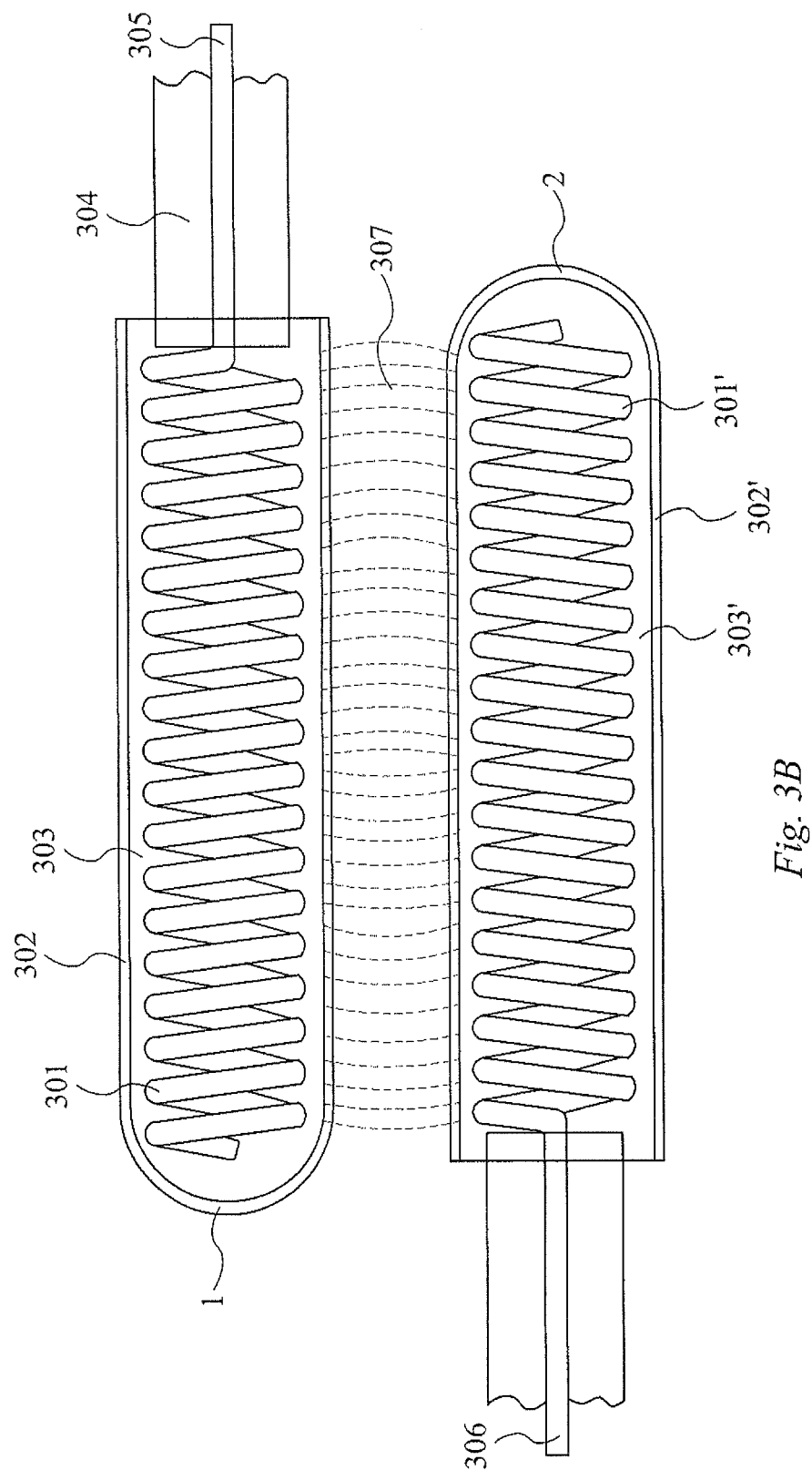

FIG. 3B shows an opposed pair of electrodes 1, 2 similar to that shown in FIG. 3A. In FIGS. 3A and 3B like reference numerals are used to indicate like elements. The electrodes 1, 2 of FIG. 3B are shown in a coplanar arrangement and each electrode 301, 302 is connected to a high voltage AC power supply via connections 305, 306.

The plasma 307 sets up between the two electrodes when the ignition voltage is reached.

The inventor in the present case has appreciated that if a plasma contacts a food product the resulting changes to the product surface resulting from the plasma are unpredictable and certain products in the pharmaceutical industry will be destroyed by direct plasma contact. The coplanar arrangement shown in FIG. 3B has the advantage that the plasma 307 generated between the electrodes need not pass through, or touch the product in the packaging and the product need not become an extension of one of the electrodes, as would be the case in a configuration in which the electrodes were arranged on either side of the product.

In addition, with coplanar electrodes it is easy to form them into an array which produces plasma on a single face and hence is easy to adapt to many applications having only to touch one side of a package with the plasma generating face to get the ozone inside the package. Moreover, with a single face array it is very convenient to retro-fit existing packaging machines and it is possible to produce a hand held device for use with large bags and irregularly shaped packaging.

The dimension for the outside diameter of the electrode outer insulating sleeve was 5 mm and the length can be chosen for the particular application without much restriction. Tests were carried out with 55 mm length electrodes in a single pair and in arrays consisting of eight pairs with 2 mm gaps between the electrodes all connected to a single power supply. The inventors in the present case have found that a gap of approximately 2 mm between the electrodes provides a surprisingly high depth of penetration of the plasma beyond the wall of the packaging material without a need to provide excessively high voltages between the electrodes.

Figure 5A:
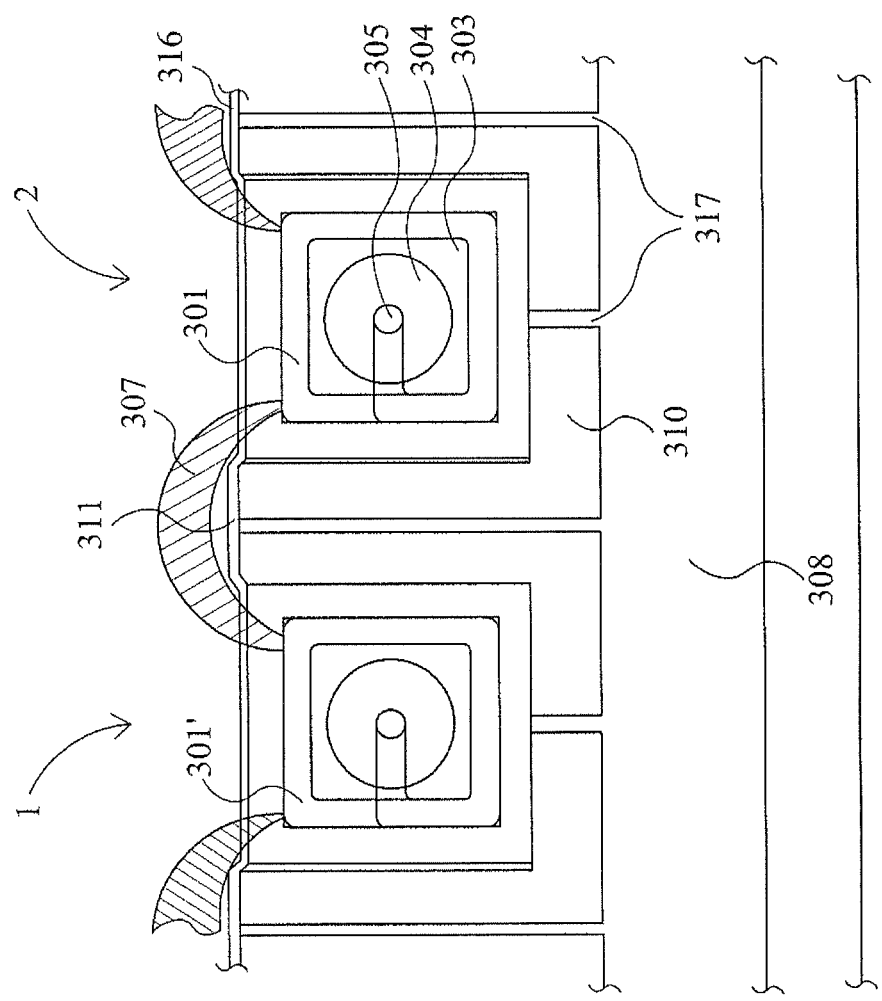
FIG. 5A shows a cross-section view of a pair of electrodes in operation.
Figure 5B:
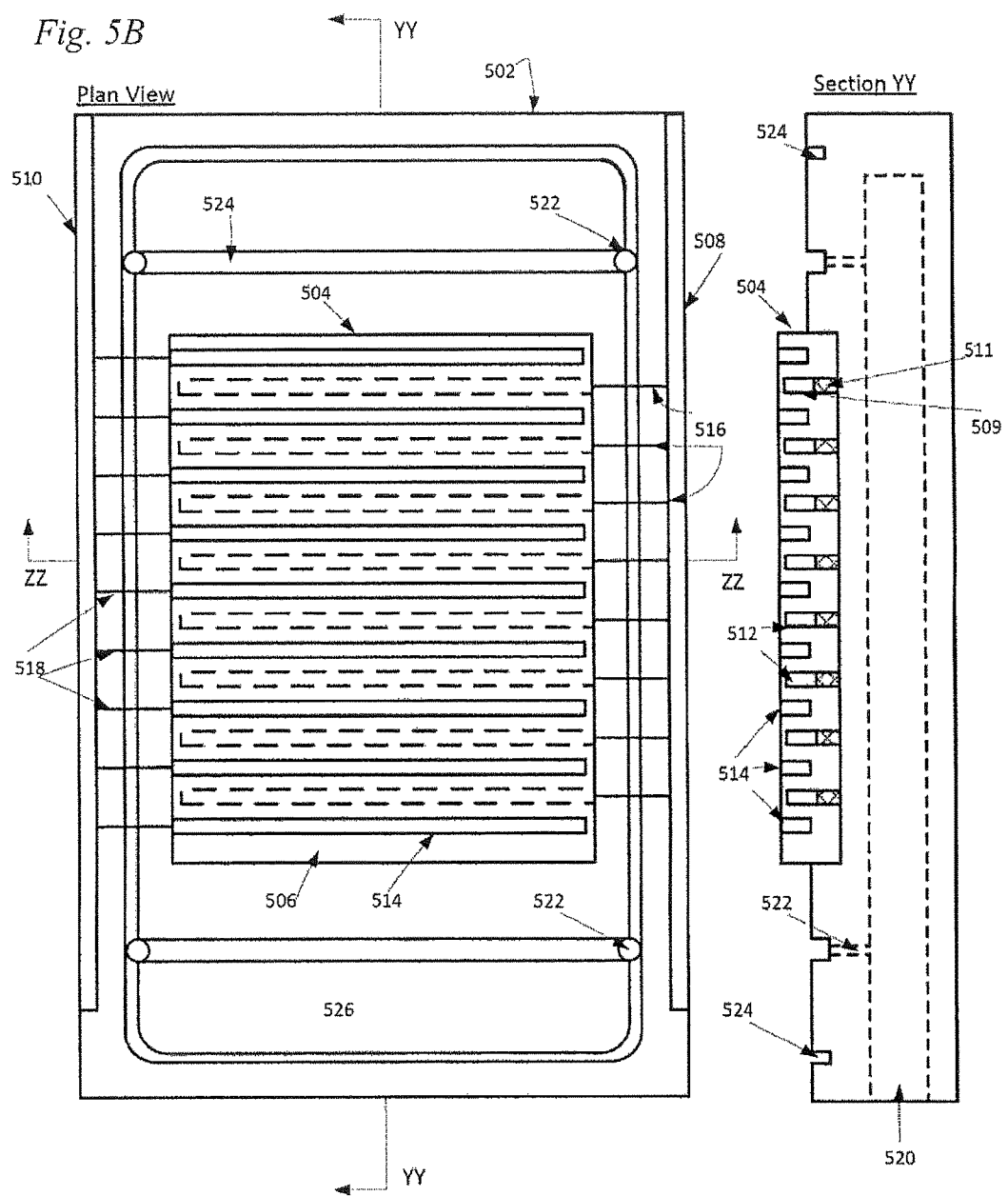
FIG. 5B shows a plan view of an electrode assembly with two sections taken along the lines indicated.
Figure 5B:
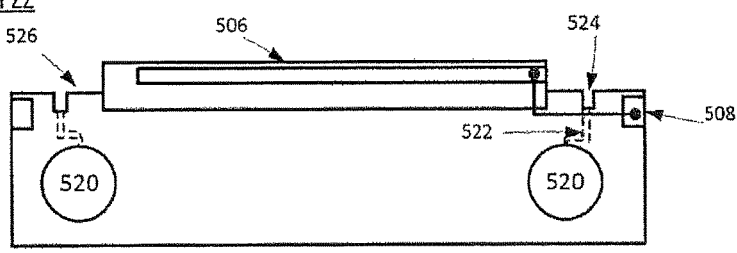

As shown in FIG. 5 a plasma is set up between each pair of electrodes and also between adjacent electrode pairs. In the example described above, the cold plasma ignition voltage was 11.1 Kv and the required power was 350 Watts. Ozone was generated at 42 ppm for a 4 second burst.

With the electrode configuration described the plasma was easily formed and was very stable. It did not seem to matter if the electrodes were moderately out of parallel alignment, the plasma formed and was stable. Surprisingly with the eight pairs of electrodes connected to one power supply all electrode pairs ignited simultaneously and the plasma was uniform and stable. Without wishing to be bound by theory it is believed that, at 40 kHz operating frequency, 8-10 kV peak AC voltage and the space between the coiled electrodes of 2 mm an antenna transmission effect is established which may contribute to the stable uniform nature of the cold plasma.

Solid electrodes were tested and cold plasma was established with this type of electrode but the cold plasma was much less stable and was much more sensitive to the uniformity of electrode spacing. Small changes in the straightness of the electrodes resulted in gaps in the cold plasma.

Figure 4A:
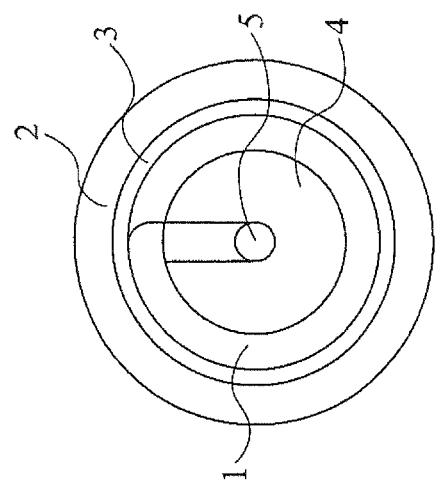
FIG. 4a and FIG. 4b show cross-sectional views of coil electrodes.
Figure 4B:
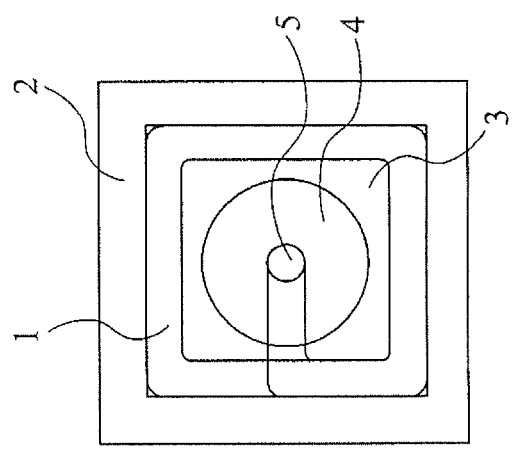

FIG. 4 shows a pair of coplanar square electrodes 1, 2 positioned in slots in an electrode holder 310. The electrodes 1, 2 are fixed such that there is an air space around the base side walls of each electrode holder 310 and so that the height of the square electrode is slightly shorter than the depth of the slot in the electrode holder so that the top of the electrode is slightly recessed into the slot. A series of small holes 317 are positioned though the centre of the slots and between the dividing walls between the electrodes. The bottom of the holes opens into a suction chamber 308 such that when suction or vacuum is applied to the suction chamber the suction draws the packaging 316 on to the face of the coplanar electrode head. Preferably the holes are conical in profile such that they become self-cleaning when the suction is in operation (any small debris or dust is easily sucked down the hole hence maintaining the suction at all time).

If the wall of a package 6 is positioned in close proximity to the front face of the electrode array it is sucked onto the face and conforms to the contours of the face forming a tight seal with no air track between the electrodes. This has the advantage that there is very little or no continuous air space between the electrodes and under the packaging material. The inventors in the present case have found that, by excluding air from these spaces plasma leakage is reduced thereby promoting penetration of the plasma through the packaging material. In this arrangement the wall of the package effectively becomes a small extension to the dielectric surrounding the electrode.

If a high voltage supply is connected to the wire contacts 305 of sufficient magnitude to ignite the cold plasma 307 the plasma forms through the packaging material 316 effectively setting up a plasma on the other side of the packaging material 316, e.g. inside the packaging. If there is oxygen on the other side of the packaging material 316 then the cold plasma will tend to convert the oxygen to ozone.

The inventor in the present case have found that, if there is a poor attachment of the packing material to the electrode array this will result in an air track under the packing material and between the electrodes. The presence of this air gap can cause the cold plasma to form in the air gap between the electrodes and not through the packing material when the power supply is connected. The inventor in the presently case has also found that, surprisingly heating of the product is prevented by more intimate contact between the packaging and the electrode. Without wishing to be bound by theory it is believed that, in the presence of an air gap between the electrodes it is necessary to apply increased power to saturate this gap cold plasma before any of it may pass through the packaging material 316 into the interior of the packaging. However the increase in power also means increased heat which if high enough will result in permanent distortion of the plastic packaging material and waste of energy.

The inventor in the present case has determined that examples of the invention produce ozone within packaging 316 without plasma ignition. If the electrode array as described is powered with an AC power supply but with a maximum voltage below the plasma ignition voltage a large amount of ozone is still produced; this is a major breakthrough. It is believed that the presence of strong electric fields in the capacitive coupling between the electrodes causes an invisible cold plasma to be formed.

With the electrode array confined to a small space inside a plastic bag and the power set at 150 watts with no ignition of the plasma the ozone reading for a 4 second burst was 100 ppm. This was repeated for the power set at 100 Watts and the ozone reading was 41.7 ppm. These tests show power reductions of 58% and 72% respectively and still producing more than enough ozone; it is expected that, in general production no more than 5-8 ppm of ozone inside a package will be needed.

As there is no ignited plasma the potential for erosion of the electrodes is substantially reduced and there is little or no heat, so the risk of overheating the plastic packaging material is reduced.

FIG. 5B shows a packet disinfection electrode assembly for use in a method of disinfecting packaged articles. Figure B includes a plan view of the assembly and two sections, one through the assembly along the line indicated YY, and another through the line indicated ZZ in the plan view.

The assembly 500 includes a dielectric body 502 and a dielectric head 504. The head 504 carries a plurality of electrodes 512, 514 arranged at a contact surface 506 of the head and is arranged so that the contact surface 506 stands proud from the body by an offset distance of at least 3 mm.

The dielectric head 504 comprises a ceramic known as shapal. The body 502 comprises another ceramic that is cheaper than shapal, and easier to machine.

Coupled to the body 502 are two conductive bus bars 508, 510. The first bus bar 508 is arranged down one side of the body 502 and the second bus bar 510 is arranged down the other side of the body. The first bus bar 508 is coupled to a first plurality 512 of the electrodes at the contact surface via conductive couplings 516 so that the bus bar can be used to apply a voltage to all of the first plurality of electrodes 512.

The second bus bar 510 is coupled to a second plurality of electrodes 514 at the contact surface 506 via conductive couplings 518.

The head 504 has a contact surface 506 and a rear surface 507 which lies adjacent the body and, in use, is hidden from view. A series of recesses 509 are machined into the ceramic of the head 504. The recesses 504 cut nearly all the way through the ceramic of the head 504 to the contact surface 506. The ceramic that separates the inside of these recesses from the contact surface 506 is 0.5 mm thick.

Each electrode of the first plurality of electrodes 512 is arranged in a recess 509 in the rear surface 507 of the ceramic of the head 504 so that each electrode 512 is separated from the contact surface by the 0.5 mm thickness of ceramic. The electrodes 512 are potted in a silicone resin and the recesses 509 are filled with the silicone resin. The contact surface 506 of the head 504 also carries a series of recesses 515 which are configured to receive the second plurality of electrodes 512. Each electrode of the second plurality of electrodes 514 is arranged in one of the recesses 515 and potted in a silicone resin. The silicone resin is removed from contact surface 506 to expose a conductive surface of the electrode in the recess. The exposed surface of each electrode of the first plurality of electrodes 514 is arranged to be flush with the contact surface 506.

The electrodes 512, 514 extend along the contact surface and are inter-digitated, e.g. interleaved, rather in the manner that the fingers of two hands can be interleaved, one between another. In this arrangement, the first and second electrodes 512, 514 are arranged so that alternate electrodes are exposed at the contact surface and alternate electrodes are insulated. The electrodes 512, 514 extend parallel with one other along the contact surface so that the spacing between the edges of the interdigitated electrodes is 3 mm and this spacing is even along the length of the electrodes.

Although the spacing between the electrodes is even along their length the electrodes 512, 514 comprise coiled conductors and so the edges of the electrodes are not straight lines but have an undulating profile, in which each undulation corresponds to a turn of the coil. Accordingly, although the spacing is even along the length, the parts of the electrodes which provide the shortest spacing (distance of closest approach) between the two electrodes may not be continuous or straight but may comprise a short discontinuous regions such as those provided by undulations associated with the longitudinal cross section of a coiled electrode.

The body 502 of the electrode assembly 500 is broader than the head 504 and so provides shoulder portions 526 around the head. These shoulder portions 526 are flat areas around the head 504. The shoulder portions 504 comprise a channel 524 which surrounds the head 504 on the shoulder portions 526.

The body 502 of the assembly 500 comprises two suction couplings 520 which are cavities extending into the body along its length. Fluid communication between the suction couplings 520 and the channel 524 is provided by a plurality of vent passages 522 which extend from the suction couplings 520 into the channel 524. The vent passages are distributed about the length of the channel 524 to enable suction to be provided evenly along the channel.

In operation the electrode assembly 500 is arranged above a receiving area in which a packaged article is received. A package to be disinfected comprising an air space is arranged so that the air space in the package is adjacent the contact surface 506 of the electrode. The package and/or electrode assembly 500 is/are urged into contact so that the package deforms to stretch a wall of the package across the contact surface 506 against the contact surface 506 of the assembly 500. In this state the package is able to create a seal with the shoulder portions 526 of the electrode assembly 500.

The air pressure within the suction coupling 520 is then reduced in order to suck the package against the shoulders and the electrode head to remove any air space from between the contact surface and the package.

An AC voltage of rms (root mean square) amplitude 10 kV and having a frequency of 40 kHz is applied across the bus bars 508, 510 so at the electrodes 512, 514 an electric field of approximately 5 Mega Volts per meter is established between the electrodes. This can form a plasma in the air space inside the package, thereby generating ozone from the oxygen in that air space. The inventors have found that voltages of approximately 10 kV and an interelectrode spacing of a few mm (e.g. 10 kV) at currents of between 2 mA and 20 mA are sufficient to generate ozone in a concentration of up to 100 ppm inside packaging. This can be achieved using pulses of electrical power over a duration of between 0.1 seconds and 10 seconds. The use of both insulated and exposed electrodes has been found to enable plasma to be set up using much less electrical power than had previously been possible. In previous embodiments powers of approximately 350 Watts were required. However, in some examples the configurations described herein enable powers as low as 80 Watts to be used. This has the advantage of reducing the possibility of damaging packaging.

The power delivered by the AC voltage may be controlled by modulating the AC voltage. A series of pulses may be used and modulation may comprise modulating the width (duration) of the pulses. The duty cycle may also be controlled to vary between a few percent, typically 3% up to about 90%. During modulation typically pulse durations of at least 0.1 seconds or as long as 0.5 seconds are used. A frequency of 30 kHz to 50 kHz is advantageous but frequencies of between 5 kHz and 100 kHz are also useful and other frequencies may also be used.

The inventors have also found that stray capacitance can cause problems in the system and one way to address this is to use a floating power supply, e.g. a power supply voltage that is not referenced to ground.

The dielectric body 502 may comprise the same material as the head 504, or may be made from a different material. The head 504 may comprise any electrical insulator and need not be a dielectric. In some cases it comprises ceramic, but this is merely preferable. Shapal is an example of a ceramic that is particularly advantageous for this use.

The head 504 is shown as carrying a plurality of electrodes 512, 514 arranged at the contact surface 506 of the head but only two electrodes are needed, one of each polarity. However, the use of multiple electrodes has been found to have certain advantages, particularly where there is a need to reduce power consumption, or to improve the efficiency of ozone production in a package.

The electrodes 512, 514 are described as being arranged along the contact surface 506. Preferably this means that they extend adjacent the surface within a few millimeters of the surface. It is not necessary that they lie precisely on or at the contact surface, although this has been found to be particularly advantageous because it promotes close contact between the electrodes, the contact surface and the package which is to be sterilized. The inventors have found that, where any air gap or evacuated space is present between the electrodes but outside the package, the efficiency of ozone production inside the package is reduced.

The head 504 is arranged so that the contact surface 506 stands proud from the body by an offset distance. The offset distance may be at least 0.2 mm, or at least 0.5 mm, or as much as 20 mm. In some cases the head 504 may not stand proud from the body 502 so that the contact surface may be flush with the body.

The bus bars 508, 510 are optional and in some embodiments each electrode may be coupled separately to a power source away from the head. The use of bus bars has the advantage that a single electrical coupling can be used to provide electrical power to all of the electrodes. Thus, if there is a need for maintenance, the electrode assembly can be removed as a single unit by simply decoupling the bus bars (and if necessary the suction system). In a production environment this may be a significant advantage because it reduces the maintenance time required because the electrode assembly can be removed and replaced simply and quickly.

The first bus bar 508 and the second bus bar 510 are shown as being arranged on opposite sides of the body 502. Although this configuration is optional it provides a number of advantages, in particular it reduces the possibility that other regions of the electrical system might be closer to each other than the electrodes, thereby providing more reliable operation.

The conductive couplings 516, 518 enable to electrodes to be coupled to the bus bars across the shoulder portions of the body 502. However, although advantageous this too is optional and in some cases some or all of the electrodes may extend to the bus bars.

Although the ceramic of the head 504 is shown as having recesses on both the contact surface 506 and the rear surface 507 this is not necessary. In some cases the recesses are provided only on the contact surface as a series of trenches. The first plurality of electrodes 512 can then be insulated by covering them with an insulator, for example shapal or another ceramic.

The electrodes are described as being potted in a silicone resin and although this too is optional it has been found to provide an advantage in that it excludes air from the region surrounding the electrode and this in turn helps to ensure that plasma is established in the airspace in the package rather than in any spaces in or around the electrode head external to the package that is to be disinfected. Although a silicone resin is useful for this purpose any suitable dielectric or non-electrically conducting medium will suffice, all that is required is a non-conductive filler that fills the space around and within the electrode.

The recesses are described as being machined/cut into the ceramic but this does not necessarily mean that they must be etched or cut out of the body of the ceramic. In some cases the ceramic may be formed or shaped with the recesses in place.

The electrodes are shown as being straight and elongate however although this has a number of advantages, not least simplicity of manufacture, other configurations may be used. For example the electrodes may be arranged as concentric rings or other shapes with an even spacing between the electrodes along any portion of their length. For example, electrodes arranged as concentric circles have the advantage of providing relatively large regions of well controlled electric field (uniform spacing) without the unpredictability/ edge effects caused by angular or discontinuous structures.

The body 502 of the electrode assembly 500 is described as being broader than the head 504 to provide shoulder portions 526 around the head, however this is optional and the shoulders need not be provided. These shoulder portions 526 may or may not comprise a channel 524, or they may comprise a plurality of channels. The channel or channels may surround the head in a continuous loop or boundary but in some cases the channel may be discontinuous or provided only along some parts of the shoulders—e.g. it may surround without completely surrounding the head. In some cases the channel completely surrounds the head.

In some cases only one suction coupling 520 is provided, for example as a single cavity in the body 500. In other cases more than two suction couplings 520 may be present. Fluid communication between the suction couplings 520 and the channel 524 may be provided by a single vent passage 522 and the vent passage or passages may extend through the ceramic body or may be provided by a tube external to the body 502. Where more than one vent passage is used the vent passages may be distributed regularly or irregularly about the length of the channel 524 to enable suction to be provided more reliably along the length of the channel.

FIG. 5C shows a plan view of the electrode assembly 500 shown in FIG. 5B with a resilient sealing member 600 coupled around the assembly. The sealing member 600 surrounds the shoulders 526 of the assembly and extends outwardly from the assembly by about 5 mm. The sealing member has rectangular cross section and stands proud of the shoulders by approximately 1.5 mm.

In use, a package to be sterilised is urged against the assembly 500, 600 so that the sealing member forms a seal with the wall of the package. Air is then evacuated from the space between the face of the assembly, and the contact surface 506 of the head 504 by drawing air out through the channel 524 and the suction couplings 520. This draws the package down on to the working surface.

The sealing member is shown as being rectangular in cross section, and this provides certain advantages but other shapes may also be used. Preferably the sealing member 600 comprises Viton, but other resilient materials may also be used. The sealing member is typically around 5 mm wide but in some cases wider or narrower seals may be used. The height of the seal is generally at least 0.5 mm measured from the surface of the shoulders, but the seal may protrude further, for example as much as 10 mm or more.

Figure 6:
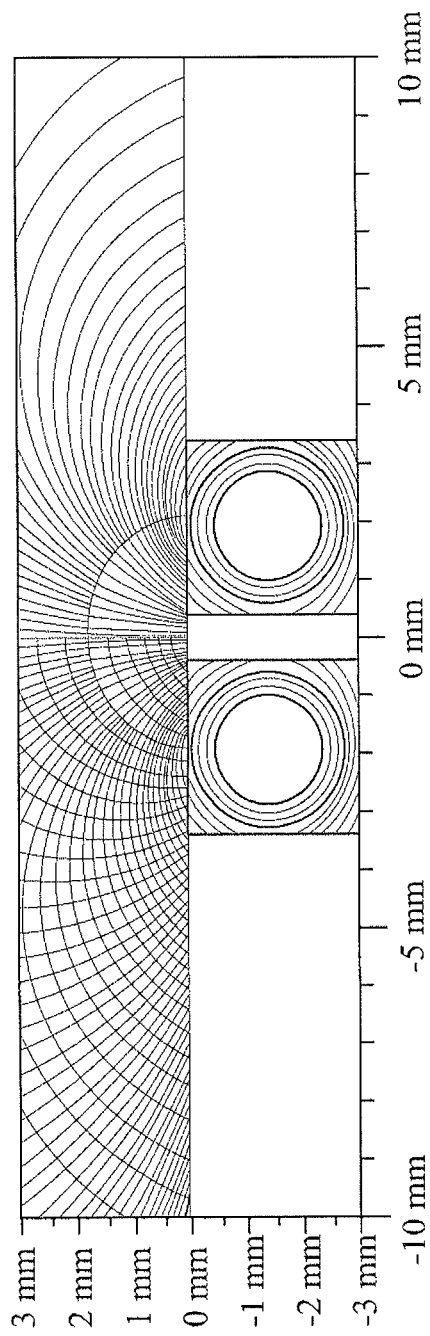
FIG. 6 shows the electric field associated with an energized round electrode pair embedded in an inserting carrier.

FIG. 6 shows an energised round electrode pair embedded in an insulating carrier and the resulting electric field. The cold plasma when ignited conforms to the equipotential lines; additional voltage magnitude results in increase in density of the cold plasma which when further increased leads to lengthening of the cold plasma band. The field plot on the left shows added field strength lines from the right hand electrode.

Figure 7:
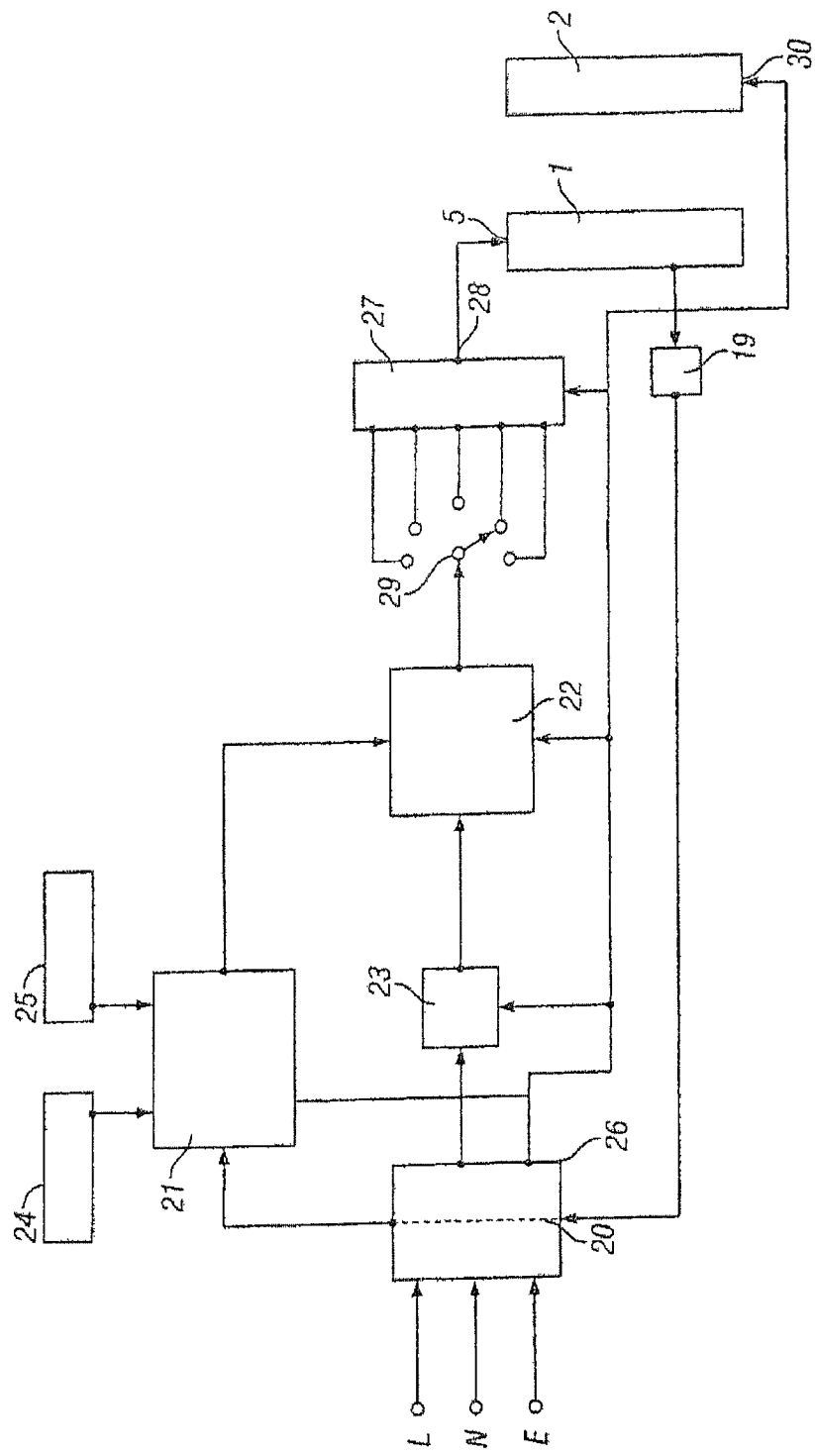
FIG. 7 is a schematic diagram of a power supply circuit of the apparatus of FIG. 1.

Referring to FIG. 7 of the drawings, there is shown a schematic diagram of one example of the high voltage power supply 18 of FIG. 1. The power supply comprises a low voltage dc power supply 20, which has the ability to automatically adjust its dc output from a signal input. The low voltage dc power supply 20 generates a low voltage supply the pulse generator 21 and a power driver circuit 22 via an EMC filter 23 which removes any high frequency interference. The pulse generator 21 has both variable pulse width control 24 and variable pulse repetition rate control 25 and supplies the drive pulses to switch the power driver device on and off in the power driver circuit 22.

Preferably the power driver device is a power MOSFET device selected to handle the power at the required drive frequency. A transformer 27, whose primary windings are switched by the power driver circuit, steps up the primary voltage to a high voltage at the output 28. Preferably the transformer is designed for high frequency operation and may comprise a high frequency autotransformer.

To enable a selection of high voltages to be generated by the transformer its primary winding is tapped such that the primary to secondary turns ratio and hence the output voltage can be altered and selected by selector 29.

The electrodes 1,2 are connected to the output terminals of the transformer via the metal contacts 5,30 and the sensor 19, which is in close proximity to the electrodes 1,2, feeds a signal back to the low voltage power supply 20. As the electromagnetic field varies the low voltage power supply 20 uses the signal to automatically adjust the magnitude, pulse width and pulse repetition rate of the low voltage fed to the primary winding of the transformer 27 therefore keeping the electromagnetic field strength substantially constant.

This method can be used with two single electrode assemblies positioned on opposite faces of the package or part of the package, so that the electromagnetic field forms between the electrodes and through the package from both sides this is an ideal solution for form, fill and seal package processes.

The power leads will have voltage potentials up to 20 kV and it can be dangerous routing cable at this high voltage especially when some of the applications require floating supplies (not connected to earth).

These power leads will also radiate high frequency interference which must be dealt with to meet international standards.

The inventor in the present case has appreciated that these problems can be addressed by designing each head so that it has it own integral transformer and then driving these transformers in parallel from a single lower voltage power supply. The high voltage power supply leads now become the same length and very short which solves the varying inductive impedance problem. The short power leads are now easy to screen to prevent RF interference and pose no danger from high voltage cabling; only the low voltage is carried any distance in a cable.

Figure 8:
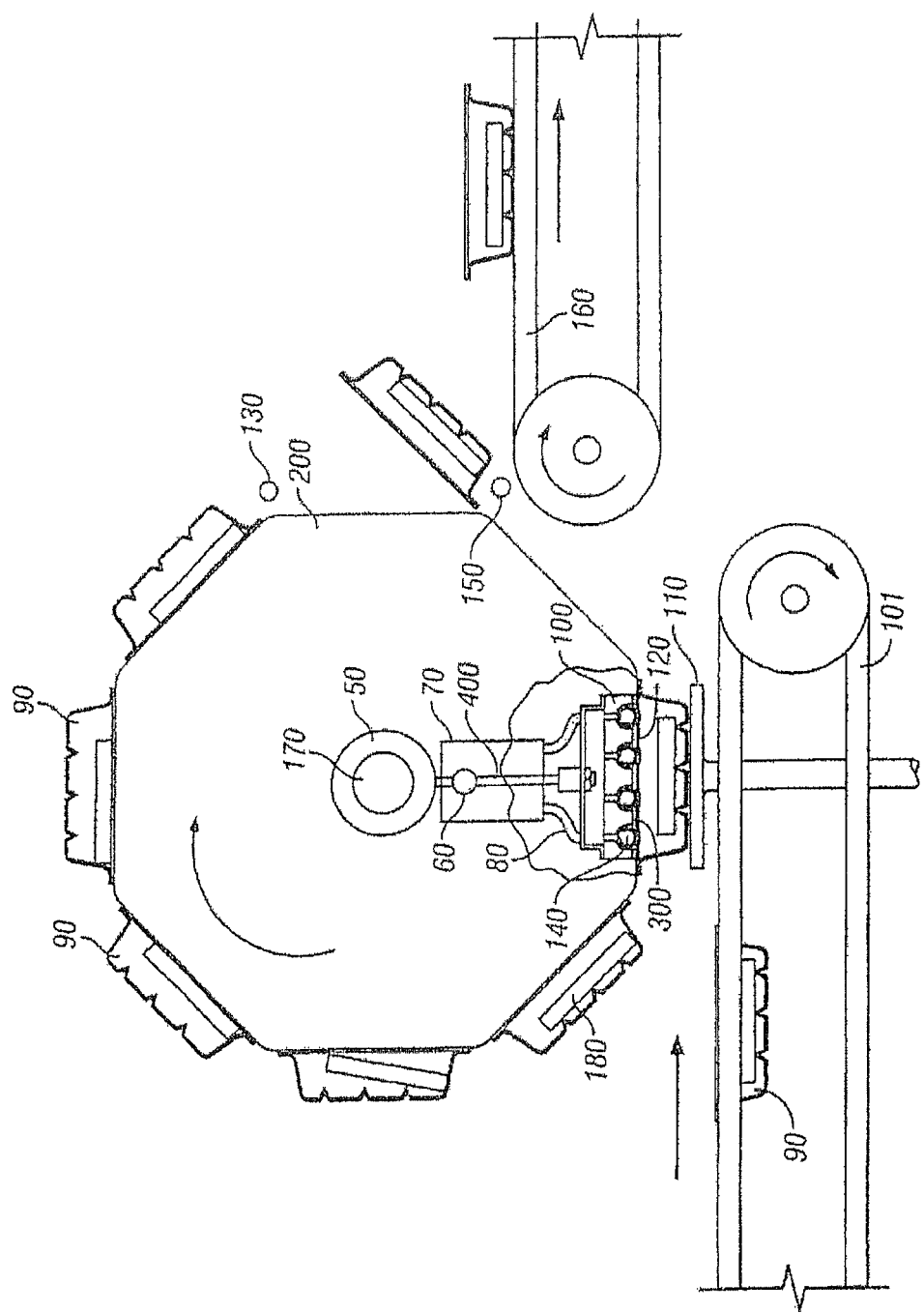
FIG. 8 is a sectional view of a disinfection apparatus.

Referring to FIG. 8 of the drawings, in and embodiment the apparatus comprises a plurality of electrode assemblies 100, 500 as described above, mounted onto a carousel 200. The carousel 200 is octagonal in shape with a eight peripheral faces, each containing one electrode assembly 1000 mounted into each of the faces of the carousel 200. Only one assembly 100 is shown in the Figure for clarity. Whilst an octagonal shape is shown for this embodiment the carousel could be many shapes with any number of faces.

Each electrode assembly 100 is positioned such that its chamber 300 projects outwardly away from the centre of the carousel 200 and forms the peripheral face of the respective face of the carousel 200. Means (not shown) are provided to make the carousel 200 rotate around a central shaft 170.

Means are provided to pass air through each electrode assembly 100 (to form suction at the front face of the chamber 300) in the form of a pipe 400 fixed to the suction chamber 300 on the discharge tube assembly 100 at one end and fixed to a suction manifold 50 at the other end via a valve 60. The valve 60 controls the suction, such that suction is applied when the valve 60 is open and vice-versa. The suction manifold 50 is fixed to a suction source (not shown) via a rotational seal.

Each electrode assembly 100 has its own high voltage power supply 70 attached to the carousel 200, which for compactness, are placed alternatively on both sides of the carousel and connected to the respective discharge tube assembly 100 by high voltage wires 80. Means to power the power supplies 70 is provided by a rotating contact assembly (not shown).

The sealed packages 90, requiring disinfection, are fed by an indexing conveyor 101 to the loading position opposite the face of the first discharge tube assembly 100. Means are provided to elevate the package 90 into position on the exit face of the first discharge tubes assembly 100 by a moveable platform 110 and a sensor (not shown) senses that the package 90 is in position.

The sensor energises valve 60 to its open condition and the resultant suction forms a tight seal between the top of the package 90 and the front face of the chamber 300; this also supports the weight of the package 90. The moveable platform 110 withdraws and the carousel 200 indexes by rotation in the clockwise direction to the second discharge tube assembly position. The package 90 is retained by the suction in position tight against the front face of the chamber 300 of the first discharge tube assembly 100 as it indexes around the carousel 200, the first discharge tubes 140 are then switched on to disinfect the package 90 and the sequence repeats.

A sensor 130 senses that a package 90 has reached a discharge position and switches off the discharge tubes 140 and the suction by opening valve 60. The package 90 having no means of support falls forward and is guided onto an exit conveyor 160 by a guide member 150.

As the packages 90 progress around the carousel 200, the product 180 inside each package continually changes position exposing surface area and encouraging the ozone to quickly disperse through the airspace. In this manner, there is a continuous disinfection process for sealed packages 90 and the carousel 200 provides an ample time delay to ensure that sufficient ozone is generated inside the package 90.

Figure 9:
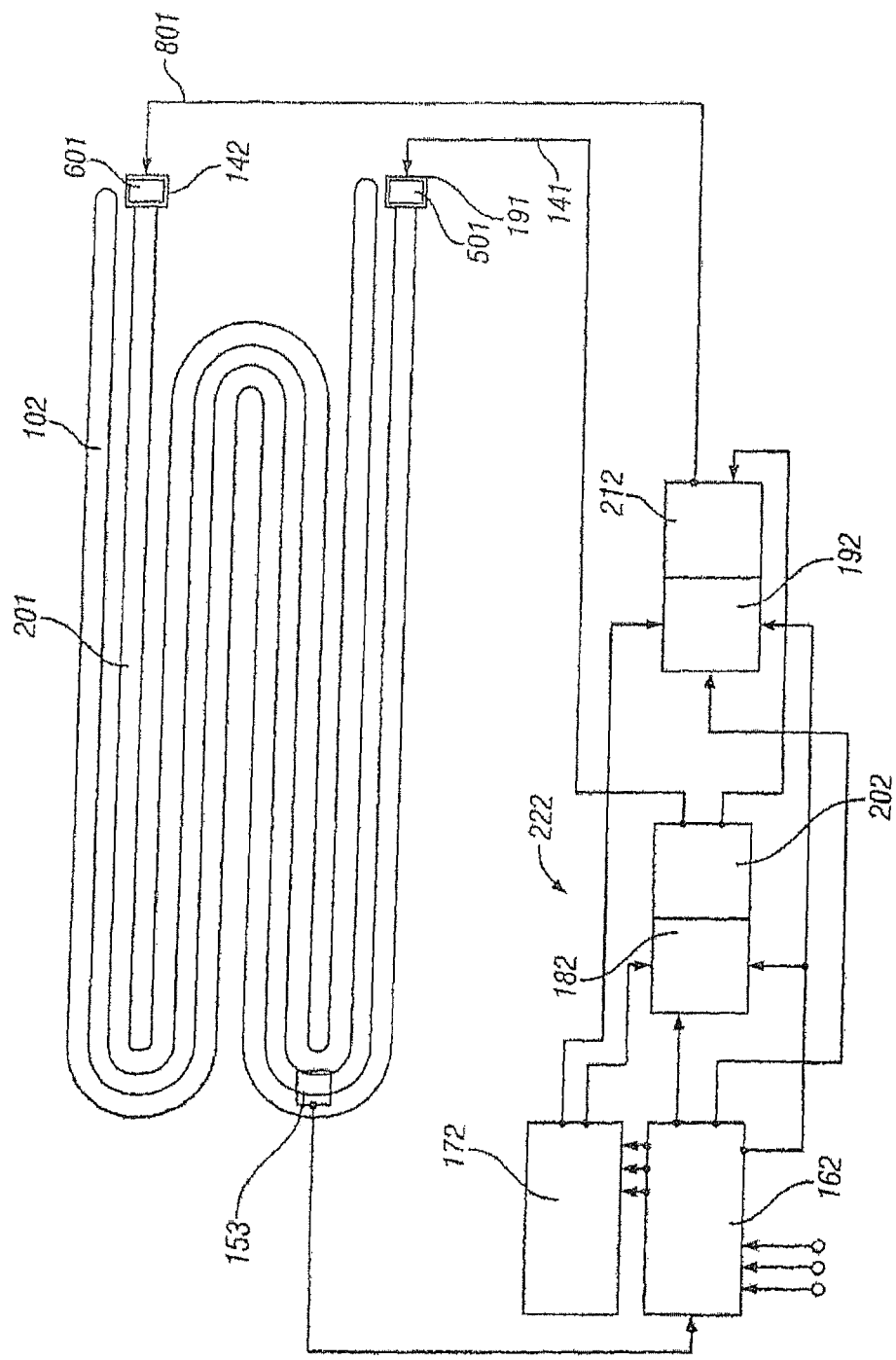
FIG. 9 is a schematic diagram of a disinfection apparatus.

Referring to FIG. 9 of the drawings, there is shown a discharge tube apparatus comprising two electrodes 102, 201 positioned in close proximity to one another. Each of the electrodes 102, 201 are made into a flat serpentine structure. High voltage wires 801,141 connected to the metal contacts 501, 601 connect the electrodes 102, 201 to the power supply 222 through suitable high voltage insulators 191, 142. The electrodes 102, 201 are positioned such that the two serpentine forms interleave in a flat plane. Each of the electrodes 102, 201 have their own power supply 182, 202 and 192, 212. The electrode 102 is powered from a positive pulsed high voltage with respect to common and electrode 201 is powered from a negative pulsed high voltage with respect to common. The positive and negative high voltage pulses may be synchronized and this may produce an efficient and very effective way of producing cold plasma containing ozone and oxygen species from air. In some instances to enhance ozone production it is desirable to alternately energise the electrodes with positive and negative pulses. The high voltage power comprises a low voltage dc power supply 162 which has the ability to automatically adjust both of its dc outputs from a signal input. The low voltage dc power supply 162 generates two low voltage supplies, one positive with respect to common and one negative with respect to common. The positive dc supply feeds the pulse generator 172 and the power driver circuit 182 and the negative dc supply feeds the power driver circuit 192. To enable the pulse generator 172 to drive both power driver circuits it has complimentary outputs as well as both variable pulse width control and variable pulse repetition rate control. These complimentary drive pulses switch the two power driver devices on and off in the power driver circuits 182,192. Preferably the power driver devices are power MOSFET devices selected to handle the power at the required drive frequency.

Two transformers 202,212 whose primary windings are switched by the power driver circuits 182,192 amplify the primary positive and negative voltages to a large positive voltage to drive electrode 102 and a large negative voltage to drive electrode 201. Preferably both transformers are designed for high frequency operation.

To enable a selection of high voltages to be generated by the transformers 202,212 their primary windings are tapped, such that the primary to secondary turns ratio and hence the output voltage ranges can be altered and selected. A field strength sensor 153 which is in close proximity to the electrode 102, 201 feeds a signal back to the low voltage power supply 162. As the electromagnetic field varies the low voltage power supply 162 uses the signal to automatically adjust the magnitude of the voltage fed to the primary windings of the transformers 202,212 therefore stabilising the electromagnetic field strength.

This present invention is applicable to the disinfection of perishable and non-perishable products in sealed packages across a wide range of applications. The following list is by no means exhaustive and includes food items, bottled drinks, bottled sauces, produce such as salad, medical tools and instruments, baby's bottles etc. Other examples and variations will be apparent to the skilled reader in the context of the present disclosure.

The invention claimed is:

1. A package disinfection apparatus, comprising:
an electrode support having a contact surface configured to contact a package to be disinfected; and
two conductive electrodes configured to receive an alternating voltage to enable generation of ozone between the electrodes such that, in use applying the electrodes to the package converts oxygen to ozone within said package,
wherein the two conductive electrodes each comprise a plurality of elongated fingers that are interdigitated at the contact surface.

2. The package disinfection apparatus of claim 1 in which at least one of the electrodes is substantially covered with an insulating material.

3. The package disinfection apparatus of claim 2 in which the electrodes comprise distributed impedances.

4. The package disinfection apparatus of claim 1 comprising a sensor for sensing pressure at the contact surface of the electrode support to enable control of the current based on the pressure.

5. The package disinfection apparatus of claim 1 in which at least one electrode is potted in an insulating material.

6. The package disinfection apparatus of claim 1 comprising a current sensor for sensing current flow between said electrodes in order to detect an over current condition and control means for preventing operation of the package disinfection apparatus in the event that an over current condition is detected.

7. The package disinfection apparatus of claim 1 wherein the two conductive electrodes are disposed in an electrode head providing the electrode support, wherein one of the two conductive electrodes is separated from the contact surface, and the other of the two conductive electrodes has a surface that is flush with the contact surface.

8. The package disinfection apparatus of claim 1 wherein the two conductive electrodes are arranged to be coplanar with each other.

9. The package disinfection apparatus of claim 8, wherein a spacing between the two conductive electrodes is in a direction coplanar with the contact surface.

10. The package disinfection apparatus of claim 9 wherein the coplanar arrangement comprises an even spacing between the two conductive electrodes at the contact surface.

11. The package disinfection apparatus of claim 1 wherein the two conductive electrodes are parallel.

12. The package disinfection apparatus of claim 1 wherein the two conductive electrodes comprise edges, and a spacing is provided between the edges, the spacing being even along at least a portion of the length of the edges.

13. The package disinfection apparatus of claim 12 wherein the spacing between the edges of the two electrodes comprises a distance of the closest approach of the edges.

14. The package disinfection apparatus of claim 1 wherein the two conductive electrodes comprise a major dimension and a minor dimension, wherein the two conductive electrodes are aligned along their major dimension.

15. The package disinfection apparatus of claim 1 wherein the two conductive electrodes comprise a first electrode comprising a plurality of electrodes elements and a second electrode comprising a plurality of electrode elements, wherein the plurality of electrode elements of the first electrode are interleaved with the plurality of electrode elements of the second electrode.

* * * * *